United States Patent [19]

Tenold

[11] Patent Number: 5,561,115
[45] Date of Patent: Oct. 1, 1996

[54] LOW TEMPERATURE ALBUMIN FRACTIONATION USING SODIUM CAPRYLATE AS A PARTITIONING AGENT

[75] Inventor: Robert A. Tenold, Goldsboro, N.C.

[73] Assignee: Bayer Corporation, Pittsburgh, Pa.

[21] Appl. No.: 289,180

[22] Filed: Aug. 10, 1994

[51] Int. Cl.⁶ .......................... A61K 38/38; C07K 1/30; C07K 1/34; C07K 14/765
[52] U.S. Cl. .......................... 514/21; 530/362; 530/363; 530/418; 530/419; 530/470; 530/829; 530/830; 530/364; 514/12
[58] Field of Search ..................... 530/362, 363, 530/364, 418, 419, 420, 829, 830; 514/12, 21

[56] References Cited

U.S. PATENT DOCUMENTS

| | | | |
|---|---|---|---|
| 3,926,939 | 12/1975 | Ivanov et al. | 530/364 |
| 3,992,367 | 11/1976 | Plan et al. | 530/364 |
| 4,156,681 | 5/1979 | Schneider et al. | 530/364 |
| 4,177,188 | 12/1979 | Hansen | 530/364 |
| 4,222,934 | 9/1980 | Hao | 530/364 |
| 4,378,346 | 3/1983 | Tankersley | 514/2 |
| 4,754,019 | 6/1988 | Gion et al. | 530/364 |
| 4,990,447 | 2/1991 | König et al. | 435/71.1 |
| 5,132,404 | 7/1992 | Ohtani et al. | 530/364 |

OTHER PUBLICATIONS

Rojas et al. "Caprylic Acid Fractionation of Hyperimmune Horse Plasma" Toxicon, 32(3) 351–363 1994.
Steinbuch et al., "The Isolation of IgG From Mammalian Sera with the Aid of Caprylic Acid" Arch Biochem Biophys 134 279–284 1969.

*Primary Examiner*—John L. Le Guyader
*Assistant Examiner*—Nancy J. Degen
*Attorney, Agent, or Firm*—James A. Giblin

[57] ABSTRACT

Highly stable plasma-derived therapeutic albumin solutions, having a turbidity level of 5 NTU or less can be made by adding sodium caprylate to Cohn fraction II+III or IV-1 effluent at relatively low temperatures. The sodium caprylate acts as a partitioning agent to separate albumin from unwanted proteins. In preferred embodiments, the albumin source solution temperature is elevated, increased in pH and reacted for approximately six hours under conditions sufficient to disrupt the initial solution colloid, and partition albumin-containing supernatant from a colloidal disperse phase, which retains unwanted globulins and manufacturing debris. Since it tends to be a scavenger molecule, albumin is selectively stabilized by diafiltration against a buffer containing sodium caprylate, thereby assuring a high albumin monomer content and low turbidity level. The amount of sodium caprylate required for selective stabilization is determined by the amount of available binding sites on the albumin molecule.

9 Claims, 1 Drawing Sheet

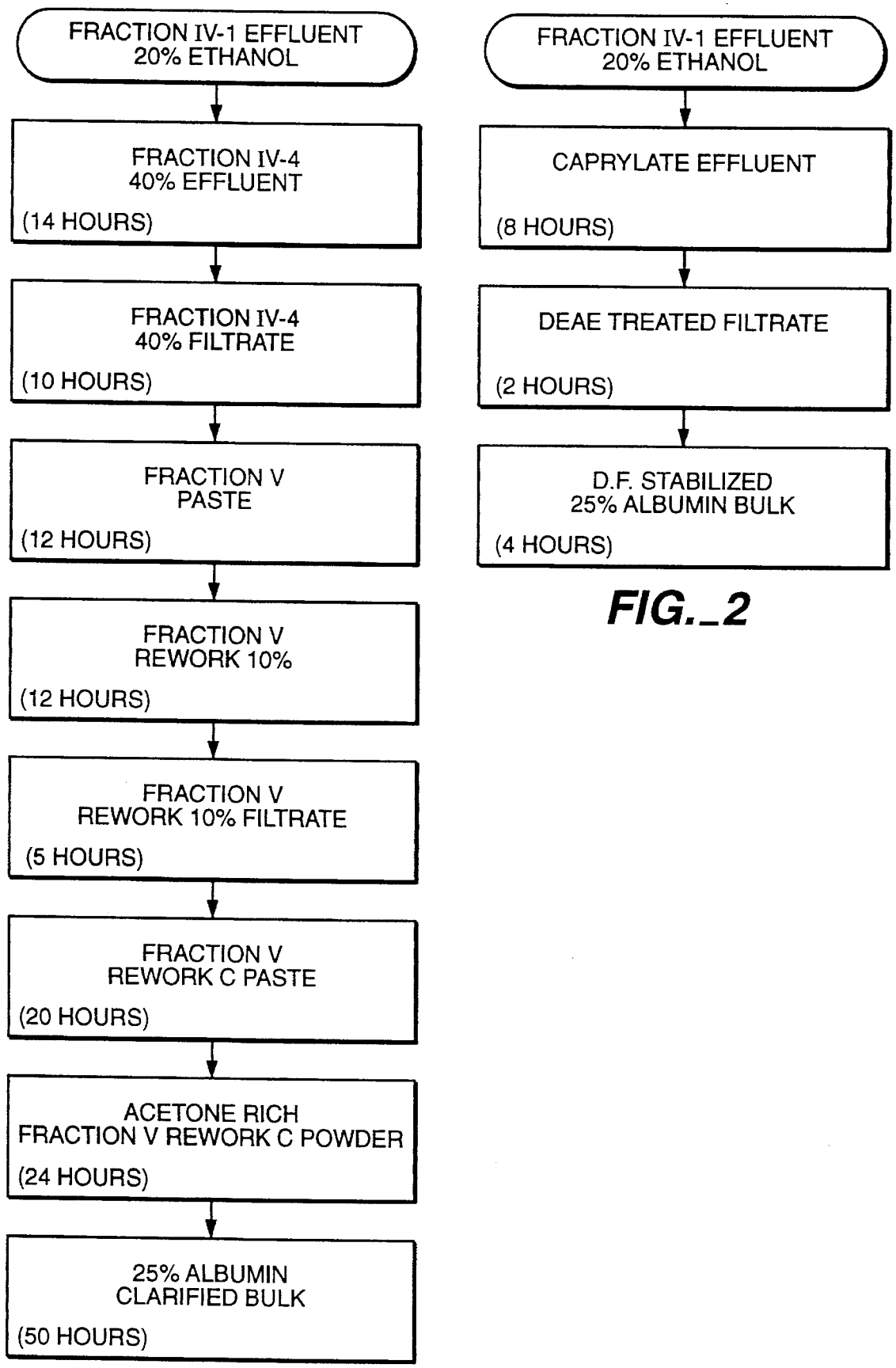

LOW TEMPERATURE ALBUMIN FRACTIONATION USING SODIUM CAPRYLATE AS A PARTITIONING AGENT

BACKGROUND OF THE INVENTION

1. Field of the Invention

This disclosure generally involves manufacturing plasma-derived therapeutic protein solutions, and more specifically, manufacturing selectively stabilized animal or human serum albumin (HSA), Alpha-1 Protease Inhibitor (Alpha-1 PI), and Antithrombin III (AT III) from serum or plasma.

2. Prior Art Description

The Cohn fractionation method, which utilizes ethanol, temperature, pH, protein concentration, ionic strength, and time to insolubilize unwanted proteins during albumin manufacture, was originally published in 1946, and remains a primary method in the United States for processing plasma. Cohn et al., *J. Am. Chem. Soc.* 68, 459 (1946). T. Gerelough's subsequent use of 95% ethanol in the Cohn fractionation process greatly diminished process volumes required, and thereby reduced corresponding manufacturing costs. Gerelough's method is also a recognized standard in the United States for plasma fractionation. U.S. Pat. Nos. 2,710,294; 2,710,293 (1955). In Europe, H. Nitschamann and P. Kistler describe a shorter method for processing albumin; however, the resulting product failed to satisfy regulatory guidelines imposed by United States agencies during that time period. *Vox Sang.*, 5, 272 (1960).

Plasma fractionation methods in the United States have employed Cohn techniques since Cohn et al's. 1946 publication. Consequently, neither interest nor necessity encouraged manufacturers to identify alternative albumin fractionation techniques for more than twenty years. M. Steinbuch, *Vox Sang.*, 23, 92 (1972). Furthermore, since conventional fractionation techniques produced albumin that could be successfully pasteurized (by heating for 10 hours at 60 degrees centigrade) to inactivate viruses, there was little motivation and much caution among albumin manufacturers in seeking alternative and improved fractionation methods.

Then in 1972 M. Steinbuch explored the ability of several reagents, other than ethanol, to separate plasma proteins via precipitation. Using Cohn Fraction III as starting material, Steinbuch studied the precipitation capacity of caprylic acid, which had previously been used to stabilize albumin (M. Steinbuch, *Vox Sang.* 23:92–106, 1972, Yu L. Hao, U.S. Pat. No. 4,222,934, 1980), and subsequently to inactivate lipid-enveloped viruses. Seng et al., U.S. Pat. No. 4,939,176, 1990. As a result of these studies, scientists later developed several techniques for purifying IgG, IgA, alpha-1 acid glycoprotein and prealbumin, concurrently finding that the precipitation reaction was highly temperature, and pH dependent.

During human immunoglobulin preparation caprylic acid is generally recognized as an effective precipitating agent for most plasma proteins at pH 4.8, so long as parameters such as temperature and ionic strength are optimized. Steinbuch et al., *Preparative Biochemistry*, 3(4), 363–373 (1973). Accordingly, Steinbuch et al. have described a method for isolating IgG from mammalian sera using caprylic acid, finding that extensive non-immunoglobulin precipitation is best obtained at slightly acidic ph, but not below pH 4.5. Steinbuch et al., *Arch. Biochem. Biophys.*, 134, 279–294 (1969).

Habeeb et al. used caprylic acid precipitation to obtain plasma-derived IgG that was free of aggregates, plasmin and plasminogen; low in anticompliment activity; and stable during storage. *Preparative Biochemistry*, 14(1), 1–17 (1984). Also, IgA has been prepared as a routine fractionation by-product from Cohn fraction III, based on IgA solubility with caprylic acid present at pH 4.8. Pejaudier et al., *Vox Sang.* 23, 165–175 (1972). Fraction III additionally provides starting material for obtaining IgM-enriched plasma fractions.

Sodium caprylate has also been used to purify albumin. According to these methods, sodium caprylate is added to process plasma, and protects albumin when the process stream is exposed to high temperatures. Extreme temperatures not only denature process stream globulins, but often generate contaminant neo-antigens. Schneider et al., U.S. Pat. No. 4,156,681 (1979); Institute Merieux, U.S. Pat. No. 3,992,367.

Cohn fraction III was also treated with caprylic acid to precipitate ceruloplasmin, an alpha globulin that facilitates plasma copper transport. Employing this technique to obtain ceruloplasmin avoided denaturation steps involving ethanol or acetone, but has been obtained in this way only from horse, mule, rabbit, goat, sheep, and baboon plasma. M. Steinbuch, *Vox Sang.*, 23, 92–106 (1972).

Currently, technical and patent literature contain numerous albumin manufacturing methods that incorporate sodium caprylate as a stabilizing agent, and purification techniques involving caprylic acid precipitation to obtain immunoglobulins from plasma-derived Cohn fraction III. However, we are unaware of disclosures employing sodium caprylate as a partitioning agent during albumin manufacture to separate albumin from unwanted globulins and manufacturing debris.

Unexpectedly, we have also discovered significant advantages in manufacturing albumin with sodium caprylate to partition albumin from unwanted material, instead of using an ethanol precipitant. First, sodium caprylate partitioning shortens conventional albumin manufacturing methods, which reduces product handling and correspondingly improves albumin recovery by 25% or more. Resulting albumin yields are essentially aluminum-free, and exhibit 97% or greater monomer levels. Second, sodium caprylate partitioning significantly reduces the time needed to complete albumin manufacture, thus reducing equipment-related manufacturing costs by at least 65%. Third, sodium caprylate partitioning improves Alpha-1 PI and AT-III yields from Cohn fraction II+III, and is generally more energy efficient than conventional methods of manufacturing plasma products. Finally, and perhaps most important, sodium caprylate partitioning significantly reduces ethanol use, and completely eliminates the use of acetone during albumin manufacture, which largely avoids polluting our environment with noxious and environmentally harmful solvent residues. Our findings are discussed and illustrated in detail below.

SUMMARY OF THE INVENTION

The invention provides a method for manufacturing essentially monomeric, aluminum-free albumin using sodium caprylate as a partitioning agent.

The use of sodium caprylate intercepts conventional plasma fractionation at either the Cohn fraction II+III or fraction IV-1 effluent step. According to the invention, sodium caprylate is added to a colloidal effluent material including the desired albumin, and the undesired non-albumin proteins and contaminants.

After temperature and pH are elevated, the mixture then incubates for approximately 6 hours, allowing sodium caprylate to act as a partitioning agent by breaking the colloid solution into a supernatant containing albumin, and a disperse phase containing unwanted non-albumin proteins (e.g., globulins), and manufacturing debris. The sodium caprylate-treated suspension is then centrifuged, and deae sephadex is added to assist in filtration. The suspension is next filtered, ultrafiltered to 12% protein, diafiltered with 0.02M sodium caprylate, harvested, and bulked for sterile filtration. When the sterile bulk passes sterility testing, the albumin is filled in final containers.

BRIEF DESCRIPTION OF THE FIGURES

FIGS. 1 and 2: Flow Charts

The figures are flow charts distinguishing the present invention from conventional albumin manufacture according to Cohn fractionation methodology. The flow chart emphasizes only those Cohn fractionation steps necessary to differentiate the disclosed, abbreviated albumin manufacturing method from protracted Cohn fractionation techniques. Processing hours for the prior art method are based on 20 Sharples centrifuges, and most other times are based on 1000 liters of in-process plasma.

DEFINITION OF TERMS

1. Partitioning Agent, as used herein, means a substance that, when added to plasma protein mixtures during albumin manufacture, generates a suspension colloid consisting of two separate phases: a supernatant that contains albumin; and an opalescent disperse phase containing agglomerated protein particles, including alpha and beta globulins.

2. Precipitating Agent, as used herein, means a substance that, when added to plasma protein mixtures during albumin manufacture, is capable of reversibly insolubilizing solution material when the solution pH is within a specific range.

3. Non-Albumin Proteins, as used herein, means all non-albumin proteins, primarily alpha, beta and gamma globulins, and acid glycoproteins.

4. Manufacturing Debris, as used herein, means non-protein contaminants, and primarily includes multivalent metal ions, such as aluminum, and manufacturing solvents, such as ethanol.

5. Albumin-Containing Solution, as used herein, means either Cohn fraction II+III effluent, or Cohn fraction IV-1 effluent.

DESCRIPTION OF THE PREFERRED EMBODIMENTS

MATERIALS AND METHODS

Materials:

1. Starting material for the disclosed invention, Cohn fraction IV-1 effluent, was produced according to the conventional Cohn plasma fractionation method, and derived from source plasma, fractionated by Miles Inc. in Clayton, N.C.

2. Source plasma was produced from fully screened plasma according to Miles' current screening procedure, which was performed within Miles' licensed Clayton, N.C. facility.

3. Only terminally-heated samples were evaluated to support this process. Those skilled in the art realize that protein shifts during the terminal treatment of pasteurization cannot be anticipated with today's testing methodology.

4. Testing required by the CBER and foreign government regulations provided final container testing criteria.

Methods:

1. Purity Determinations
   A. Cellulose Acetate Electrophoresis (CAE) was used to the presence of proteins other than albumin.
   B. High Performance Liquid Chromatography (HPLC) was used to determine the presence of aggregates, and other protein molecular weights.
   C. Albumin filtrate turbidity was measured in National Turbidity Units using a Hach nephelometer.

EXAMPLE I

The improved albumin manufacturing method begins with four standard Cohn fractionation steps. First, human plasma is pooled, thawed, and centrifuged. The formed cryoprecipitate is harvested and processed to produce factor VIII concentrate, while the effluent's temperature is reduced to about minus 2 degrees centigrade while adding 95% ethanol containing pH 4.0 acetic acid buffer (Buffer A).

When alcohol addition is complete, the resulting suspension, Cohn fraction I, is approximately 8% ethanol by volume, and at pH 7.3 when diluted 1:5 with saline or distilled water. A majority of plasma fibrinogen is precipitated within a two hour reaction period.

Fraction I 8% is centrifuged to remove the formed solids. The effluent Fraction I is then brought to Fraction II+III 20% by the slow addition of ethanol containing buffer A, and the material's temperature is lowered to about minus 5 degrees centigrade. The final plasma pH is about 6.8. After an approximate 2 hour reaction time, Fraction II+III 20% is centrifuged, and crude II+III paste containing the gamma globulin fraction is isolated. This paste is later processed to manufacture IGIV and ISG.

The resulting Cohn Fraction II+III effluent is next treated with cold acetic acid buffer, reaching a suspension pH of about 5.2 when diluted 1:10 with distilled water. Effluent is incubated for about a 6 hour reaction period, which incorporates precipitation and denaturization. Then alpha globulins and other insoluble proteins are harvested, and the resulting precipitate is used to manufacture Alpha-I PI and AT III.

According to conventional fractionation methods, Fraction IV-1 effluent is further processed to Cohn Fraction IV-4, primarily to remove heat unstable alpha and beta globulins, and then undergoes four subsequent ethanol precipitations before either acetone drying, lyophilization, thin film evaporation, or ultra and diafiltration.

According to the present invention, sodium caprylate is next added to Cohn fraction IV-1 effluent, which insolubilizes alpha and beta globulins by wetting, or partitioning albumin from these unwanted proteins. Sodium caprylate also functions as an antiviral agent, and additionally permits mechanical separation of albumin.

Approximately 10 grams of sodium caprylate per liter is added to fraction IV-1 effluent, which is heated to about 25 to 35 degrees centigrade while simultaneously increasing solution pH to about 5.4 to 5.8. The reaction is completed within a time period of 6 or more hours, during which the pH is maintained at about 5.3 to 5.6, but preferably at 5.4.

Increasing the solution's temperature helps dissolve sodium caprylate to complete the reaction. Increasing the pH improves albumin recovery since pH levels lower than about 5.4 approach albumin's isoelectric range, which is less than the preferred pH, and subsequently could result in albumin loss. However, a pH level greater than about 5.8 may solubilize heat unstable globulins, and thus permit their escape into the final product. Total incubation time following sodium caprylate addition is approximately 6 hours.

The sodium caprylate-treated solution is then cooled to about 18 degrees centigrade or colder to inhibit bacterial growth, and centrifuged. Afterwards, about 1 gram of Deae Sephadex is added to the effluent to aid filtration. The caprylate effluent is then clarified through 0.2 micron depth and membrane filters, which produce the deae filtrate. (See FIG. 1). The resulting filtrate pH is then increased to neutrality (pH 6.8 to 7.2) with sodium carbonate.

According to conventional methods, when acid filtrate pH is increased to neutrality, solution turbidity improves. Turbidity levels of 12 NTU and higher commonly occur at pH 5.5, and decrease to about 8 NTU when pH is elevated above 5.5. This phenomena is caused by departing from the contaminating globulin's isoelectric point.

However, according to the disclosed invention, Deae filtrate turbidities are about 3 NTU or less, and when pH is elevated to 6.8, there is no significant turbidity level change, even after 10 or more hours at 60 degrees centigrade.

Thus, increasing the sodium caprylate-treated filtrate pH to neutrality does not affect turbidity levels. Rather, filtrates resulting from sodium caprylate-treated IV-1 effluent maintain a turbidity level of 5 NTU or lower, even at an elevated pH, since filtrates are essentially free of contaminant globulins after incubation with sodium caprylate.

The Deae-Sephadex clarified filtrate is then ultrafiltered with Rhomicon-type ultrafilters, and diafiltered against at least seven volume exchanges of sodium caprylate diafiltration buffer to remove metal contaminants, ethanol and salts. The diafiltration buffer is prepared according to the final container albumin concentration. For instance, if the desired final albumin concentration is 25%, then 0.02M sodium caprylate diafiltration buffer is used. If the final albumin concentration is to be 5%, 0.004M sodium caprylate diafiltration buffer is needed. Using 30,000 molecular weight (MWCO) ultrafiltration media provides excellent flux rates.

Albumin is then ultrafiltered using conventional techniques to achieve the desired final container albumin concentration. The target concentration must be sufficient to permit an equipment rinse down with diafiltration buffer and thereafter yield 25%, 20%, 7% or 5% final albumin concentrations. Finally, the concentrate is sterile filtered, bulked for release testing, and filled into final containers.

Among the many conditions affecting this invention are temperature, pH, sodium caprylate concentration, and reaction time. An experiment was conducted on Cohn fraction effluent IV-1, varying one parameter at a time to establish the ideal temperature of the caprylate reaction. Temperatures in the range of twenty degrees centigrade were tried and found to produce a turbid final container. Also, a reaction time of six hours was determined arbitrarily, since processing large albumin volumes requires varying time needed to complete the reactions. The invention was dependent on the aforementioned tests, and the effects of heat on albumin.

EXAMPLE II

Bench lots were composed of 100 to 200 liters of Cohn Fraction IV-1 effluent. Several bench lots were processed to achieve desirable parameters. The final test of acceptance was based on turbidities after the albumin was heated 10 hours at 60 degrees centigrade.

A scaled up lot of albumin was processed from Cohn Fraction IV-1. In this lot, 1100 liters of effluent Cohn Fraction IV-1 was processed to 25% albumin final containers using the method described in Example 1.

RESULTS

The process herein described yielded the following data with scale up:
Protein Concentration: 24.03% Protein
CAE: 100% Albumin
pH: 6.78
Heat Stability Duplicate
(50 Hours@57): Pass
Aluminum: 7.53 ppb
PKA: 1% Of Reference
Citrate: Less Than 5 ppm
Turbidity: 2.6 NTU
Sodium: 152 Meq/L
HPLC:
   Monomer: 97.58%
   Dimer: 2.42%
Viscosity: 7.98 CPS
Density: 1.0699
Pyrogen (3 Rabbits): 0.2 Total Of All
Caprylate: 0.086M Selectively Bound*
* A two volume CWFI diafiltration would reduce this level to about 0.07 molar.

DISCUSSION

We have demonstrated that human serum albumin, a widely used therapeutic reagent, can be manufactured faster, more efficiently, and for less money by using sodium caprylate to partition albumin from unwanted proteins and manufacturing debris. Additionally, sodium caprylate albumin fractionation as described here avoids the use of solvents such as acetone, thus avoiding polluting the environment with chemical solvents; reduces manufacturing and equipment costs; decreases albumin final container production time; and increases the yield of albumin, and other plasma-derived products such as Alpha-1 PI and AT III.

Furthermore, we discovered that albumin naturally selects and binds, through molecular attraction, the amount of sodium caprylate retained in final albumin solutions. Following sodium caprylate addition, the albumin solution's turbidity level remains below 5 NTU even after subsequent filtration, ultrafiltration, diafiltration, and pasteurization at 60 degrees for 10 hours. Consequently, sodium caprylate enhances product stability during the manufacturing process, as evidenced by low turbidity levels after adding sodium caprylate; and protects albumin from thermal breakdown during terminal high heat pasteurization, which prevents increasing turbidity during long-term storage.

Conventional albumin manufacturing methods commonly employ acetyl-dl-tryptophan, a suspected carcinogen, or sodium chloride to stabilize albumin. However, neither the tryptophan nor sodium chloride are capable of enhancing both short, and long-term albumin stability. Albumin does not bind to tryptophan, but tryptophan nonetheless protects albumin's structural integrity during exposure to high temperatures. Conversely, albumin binds strongly to sodium chloride, but sodium chloride fails to protect albumin during exposure to high temperatures. Thus, in addition to partitioning albumin from unwanted material, sodium caprylate serves the dual function of improving and maintaining albumin stability both during, and after the manufacturing process.

In light of the examples and discussion above, several potential modifications and variations of the disclosed invention will occur to those skilled in the art. Consequently, the examples provided merely illustrate the invention, which should be limited only by the following claims.

We claim:

1. In a method of preparing albumin from a solution of plasma proteins that contains albumin, non-albumin proteins and contaminant manufacturing debris including metal ion contaminants, ethanol and salts, the improvements comprising the steps of
    (a) employing sodium caprylate in the solution of plasma proteins at a pH of about 5.25 to 5.6 as a partitioning agent to separate albumin from the non-albumin proteins;
    (b) separating the albumin of step (a) from the non-albumin proteins; and
    (c) diafiltering the separated albumin of step (b) against sodium caprylate diafiltration buffer to remove metal ion contaminants, ethanol and salts.

2. The method, according to claim 1, wherein sodium caprylate is added to the solution of step (a) at a temperature ranging from about 20 to 30 degrees centigrade.

3. The method, according to claim 2, where in the sodium caprylate-treated solution of step (a) is incubated for a period ranging from about 2 to 8 hours.

4. The method, according to claim 1, wherein sodium caprylate is added to the solution of step (a) in an amount ranging from about 0.04M to 0.08M sodium caprylate.

5. The method, according to claim 1, wherein said solution of plasma proteins is brought to a pH level between about 5.4 and 5.6, elevated to a temperature between about 20 and 30 degrees centigrade, and mixed while sodium caprylate is added to achieve a concentration of between about 0.04M to 0.08M, and incubated for a period of between about 2 to 8 hours.

6. The method of claim 5 wherein the solution of step (a) is brought to about pH 5.4, heated to about 30 degrees centigrade, treated with approximately 0.06M sodium caprylate and incubated for about 6 hours.

7. The method, according to claim 1, wherein said solution of plasma proteins comprises either Cohn fraction II+III effluent or Cohn fraction IV-1 effluent.

8. The method, according to claim 1, wherein said solution of plasma proteins comprises Cohn fraction IV-1 effluent.

9. The method, according to claim 1, wherein the solution of plasma proteins comprises Cohn fraction II+III effluent.

* * * * *